United States Patent
Ogburn et al.

(10) Patent No.: US 6,936,784 B2
(45) Date of Patent: Aug. 30, 2005

(54) ILLUMINATION SOURCE FOR SORTING MACHINE

(75) Inventors: Robert Ogburn, Needville, TX (US); Klaus Oestreich, Needville, TX (US); Jeff Pawley, Sugar Land, TX (US)

(73) Assignee: Satake USA, Inc., Houston, TX (US)

( * ) Notice: Subject to any disclaimer, the term of this patent is extended or adjusted under 35 U.S.C. 154(b) by 228 days.

(21) Appl. No.: 10/444,195

(22) Filed: May 23, 2003

(65) Prior Publication Data

US 2003/0221998 A1 Dec. 4, 2003

Related U.S. Application Data

(60) Provisional application No. 60/383,727, filed on May 28, 2002.

(51) Int. Cl.$^7$ ................................................ B07C 5/01
(52) U.S. Cl. .................... 209/576; 209/577; 209/579; 209/580; 209/638; 209/639; 209/631; 209/644
(58) Field of Search ................................. 209/576–582

(56) References Cited

U.S. PATENT DOCUMENTS

| | | | | |
|---|---|---|---|---|
| 2,646,880 A | * | 7/1953 | Frankel | 209/581 |
| 2,776,747 A | * | 1/1957 | Van Douwe | 209/581 |
| 4,186,838 A | * | 2/1980 | Levitt et al. | 209/581 |
| 4,271,968 A | * | 6/1981 | Mehrkam et al. | 209/564 |
| 4,280,625 A | * | 7/1981 | Grobbelaar et al. | 209/582 |
| 4,356,921 A | * | 11/1982 | Fraenkel | 209/576 |
| 4,630,736 A | * | 12/1986 | Maughan et al. | 209/587 |
| 4,951,825 A | * | 8/1990 | Hawkins et al. | 209/558 |
| 5,148,923 A | * | 9/1992 | Fraenkel et al. | 209/539 |
| 5,201,576 A | | 4/1993 | Squyres | |
| 5,586,663 A | | 12/1996 | Graudejus et al. | |
| 5,683,961 A | * | 11/1997 | Caulder et al. | 504/130 |
| 5,745,176 A | | 4/1998 | Lebens | |
| 5,779,058 A | * | 7/1998 | Satake et al. | 209/581 |
| 6,013,887 A | * | 1/2000 | Satake et al. | 209/581 |
| 6,100,488 A | * | 8/2000 | Satake et al. | 209/580 |
| 6,234,317 B1 | | 5/2001 | Sommer | |
| 6,238,060 B1 | | 5/2001 | Bourn et al. | |
| 6,355,897 B1 | | 3/2002 | Bjork | |

* cited by examiner

Primary Examiner—Donald P. Walsh
Assistant Examiner—Jonathan R Miller
(74) Attorney, Agent, or Firm—Kenneth A. Keeling; James E. Hudson, III; Keeling Hudson, L.L.C.

(57) ABSTRACT

An illumination source for a machine vision viewer for a sorter that provides a flow of articles along a scan line includes an elongated, cylindrical shroud with illumination sources mounted interior of the shroud. The illumination sources are arranged longitudinally within the shroud and are angularly spaced along the inner circumference of the shroud. Linear slots running parallel with the shroud axis are provided in the shroud for the subject articles to enter and exit the shroud. A linear slot running parallel with the shroud axis is provided for receptors to view the articles passing through the shroud. The cylinder interior is otherwise uniform and light reflecting. An alternative embodiment of the shroud comprises two shroud arc components with openings between the arcs to allow articles to pass between the shroud arc components.

36 Claims, 4 Drawing Sheets

ILLUMINATION SOURCE FOR SORTING MACHINE

CROSS-REFERENCE TO RELATED APPLICATIONS

This application claims the benefit of U.S. Provisional Application No. 60/383,727, filed on May 28, 2002.

STATEMENT REGARDING FEDERALLY SPONSORED RESEARCH OR DEVELOPMENT

Not Applicable.

BACKGROUND OF THE INVENTION

1. Field of the Invention

This invention relates generally to sorting machines and particularly to an illumination source for a machine vision system.

2. Description of the Related Art

Sorting machines incorporating machine vision systems typically identify and sort articles by means of reflected energy waves. One of the main components of a vision machine system is the illumination source. The illumination source provides a starting point for the reception quality of the vision system. Typically, the source is required to be uniform and have a high intensity at the object point (sometimes referred to as the scan line) of the vision system. Most inspection systems include some sort of light source. Conventional light sources include incandescent and fluorescent lamps and light emitting diodes. Various optical arrangements have been designed for better illumination, such as ringed lamp arrays, focused filament projectors, and fiber optic emitters. Uneven illumination in conventional illuminators may result in detection of shadows as defects. While the characteristics commonly measured incorporate light sources including human-visible light sources, machine vision systems may measure energy waves outside the human-visible range.

U.S. Pat. No. 6,355,897 to Bjork describes an arrangement and method for sorting granules that includes a light detector arranged over a transparent pellet transportation track and a light source arranged on the opposite side of the track. The detector is at one end of a chamber with the light source and track at the other end. The chamber is evenly illuminated and may have a reflective layer. The light source may also illuminate the pellets from above or around the track. Defects are indicated as a lower intensity potential at the detector.

U.S. Pat. No. 5,201,576 to Squyres discloses a spherical chamber, which is covered with a reflective interior surface, with a light source within the chamber. A transparent tube extends through an axis of the chamber. The objects to be inspected are transported through the tube. At least two viewing openings are provided in the chamber with inspection cameras oriented through the viewing openings. The patent discloses the use of an acrylic white paint manufactured by Krylon, and claims that product's capacity to provide reflectivity above 90%. The patent further discloses use of titanium oxide coating as being prior art in optical integrating spheres.

The chamber is provided with a circularly tubular lamp, two video cameras and a transparent, cylindrical tube having two open ends. The objects are conveyed through the tube, illuminated by the lamp and examined by the cameras. One problem that may occur in connection with this solution is it may be difficult to adjust the cameras without affecting the light distribution inside the chamber. This is due to the fact that the intensity from the lamp, which is described in the U.S. Pat. No. 5,201,576, will vary inside the chamber, due to the fact that the intensity is higher close to the lamp than at a certain distance from the lamp. Another problem may be that the tube affects the light refraction in the form of reflections, e.g., that a mirror image of the lens may appear. Additionally, this solution is limited to inspecting serial objects, one side at the time.

U.S. Pat. No. 6,238,060 to Bourn et al. describes a ring light source of light emission diodes or similar points of light for providing focused, uniform light without shadows on a spot where an object may be inspected. The patent shows many variations; however, none is believed appropriate for a long scan line.

U.S. Pat. No. 6,234,317 to Sommer describes a number of light sources each within a light-transmissive cylinder that can be wiped or pneumatically cleaned from time to time. The objects pass between the light-transmissive cylinders during the inspection process.

U.S. Pat. No. 5,745,176 to Lebens describes a source having a linear array of lights and a focusing element intermediate the light source and the object to be viewed for producing a focused light on the object. The source has a background that prevents internal reflections that would otherwise interfere with the focused light and produce variations in light intensity from the source. The object that is inspected is not a moving object.

U.S. Pat. No. 5,586,663 to Graudejus, et al. describes a rotating background that can be kept clean. However, it is not a cylinder that surrounds the path of the inspected objects.

It would be an improvement to the prior art to provide an illumination system for a machine vision system that provides intense, even illumination of the articles to be viewed along a linear or elongated scan line, thereby providing consistent identification of selected characteristics and substantially reducing mis-characterization of articles as having occlusions or other defects genuinely caused by shadows.

SUMMARY OF THE INVENTION

The present invention comprises an illumination source for a machine vision viewer for a sorter that provides a flow of objects along a scan line. The present invention includes an elongated, cylindrical shroud structure with illumination sources mounted interior of the shroud. Illumination sources may include fluorescent lamps, arc lamps, gas discharge lamps, an array of filament light sources or semiconductor light sources. The sources are arranged longitudinally within the shroud and are angularly spaced along the inner circumference of the shroud.

A linear opening is provided in the shroud parallel to the shroud axis for the subject objects to enter the shroud and a second linear opening, parallel to the shroud axis, is provided to allow the objects to exit the shroud. A linear viewing opening, parallel to the shroud axis, is provided for detectors to view the objects passing through the shroud. The cylinder interior is otherwise uniform and light reflecting.

The diameter of the cylinder is limited to the minimum size practicable to maximize illumination intensity at the scan line and to allow placement of ejectors as close as practicable to the scan line to allow more accurate rejection of selected articles. However, the cylinder diameter must be large enough to reduce unwanted effects of removed cylinder surface in the area of the openings.

To further improve uniformity of illumination, the cylinder may be longer than the required passage area and the shroud ends may be closed. The entire inner surface of the cylinder section and shroud ends are finished using a material that has spectral properties suitable for optimal reflection of the illumination energy within the cylinder section and that provides maximum contrast of the objects to be sorted.

DETAILED DESCRIPTION OF THE INVENTION

Figure 1:
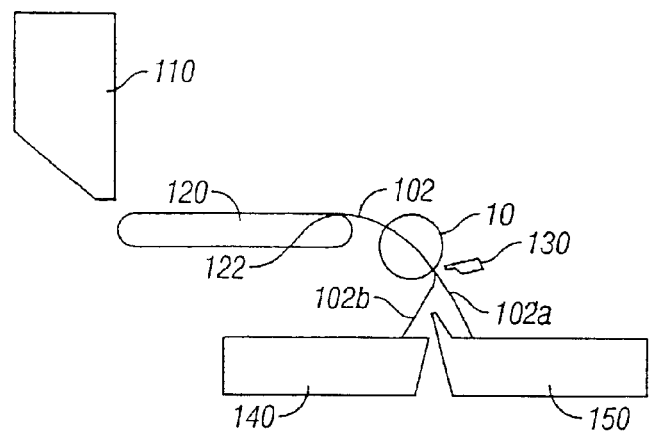
FIG. 1 depicts a machine viewing system including the illumination system of the present invention.

Referring first to FIG. 1, an illustrative machine vision sorter system 100 including the illumination system 10 of the present invention is depicted. The machine vision sorter system 100 includes a hopper 110, a conveyor 120, a vision system 10, a selector 130, a container 140 for segregated articles and a bin 150.

The articles to be viewed and sorted by the machine vision sorter system 100 of the present system are retained in hopper 110 and are dispensed onto conveyor 120. Conveyor 120 may include vibration means (not shown) to segregate individual articles (not shown) to be viewed and sorted. Conveyor 120 may additionally include tracks or channels (not shown) in addition to or as an alternative to the vibration means for segregation of articles.

Figure 2:
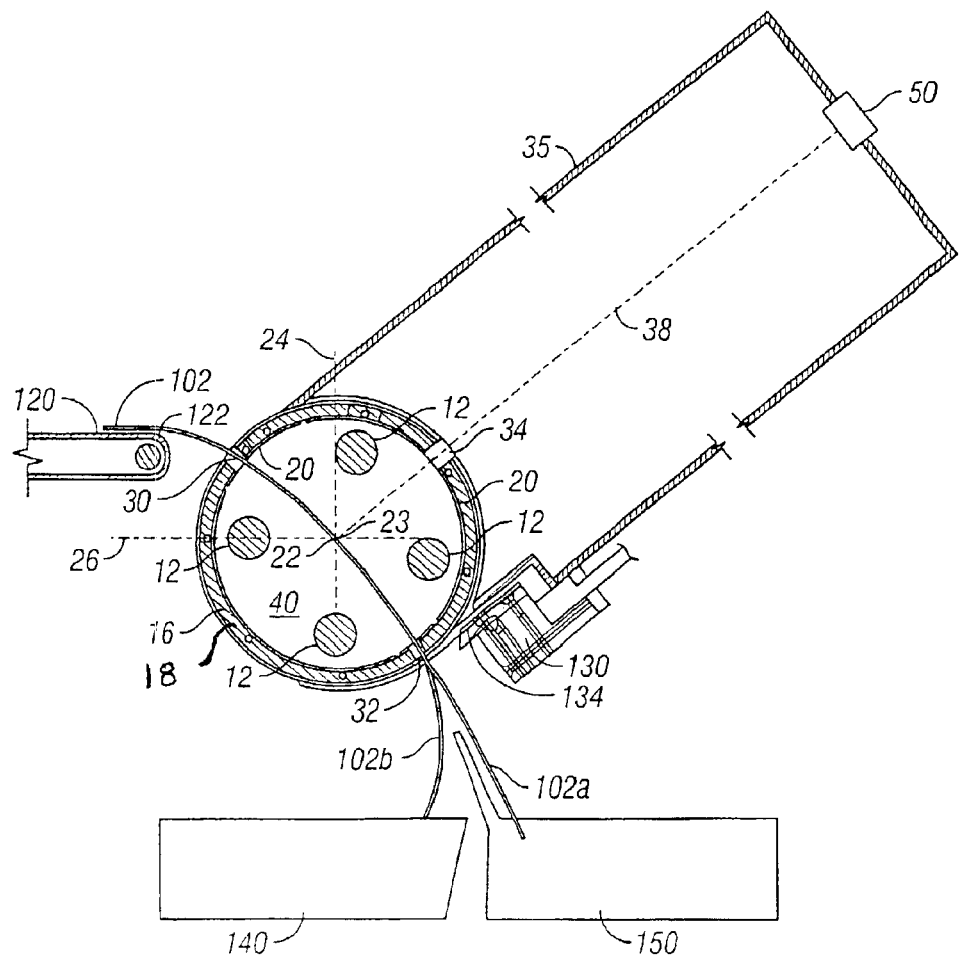
FIG. 2 depicts a cross-sectional view of the illumination system of the present invention.

In the exemplary machine vision sorter system 100, the articles to be sorted are transmitted over a shoulder 122 of the conveyor 120. The conveyor 120 is structured to provide a flow of articles from conveyor 120 with a velocity such that the articles uniformly pass through illumination system 10. The flow path of articles through illumination system 10 is represented by article trajectory 102. The machine vision sorter system 100 of the embodiment disclosed in FIGS. 1 and 2 provides for free fall of the articles upon ejection from conveyor 120. Such flow of articles defines article trajectory 102.

Figure 3:
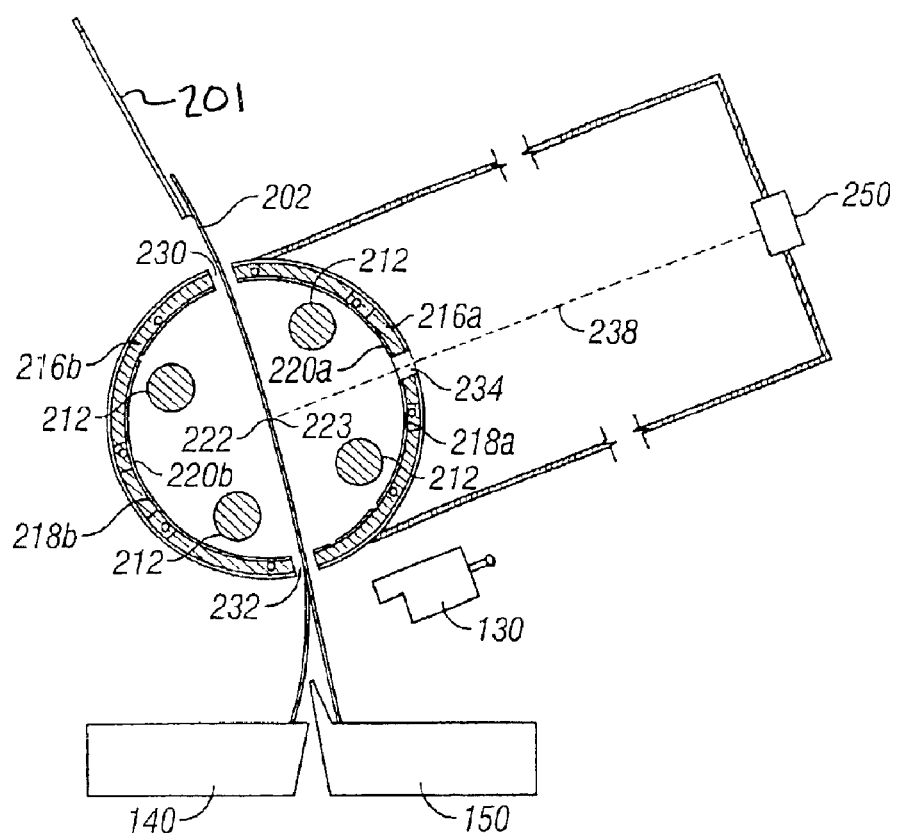
FIG. 3 depicts a cross-sectional view of an alternate embodiment of the illumination system of the present invention.

The embodiment of machine vision sorter system 100 depicted in FIG. 3 includes a gravity slide 201. In such embodiment, the gravity slide 201 is located intermediate a vibratory feeder (not depicted in FIG. 3) and the vision system 10. In such instance, the free flow of articles from gravity slide 201 defines article trajectory 202.

The articles may be any of a plurality of organic or inorganic objects, such as, for example, grains, nuts, plastic pellets. The articles may be viewed and sorted based on various criteria determined by the user, including size, color, defects and other characteristics.

Referring to FIG. 2, the illumination system 10 of the present invention includes an elongated, cylindrical shroud 16. Cylindrical shroud 16 includes shroud wall 18 having an inner reflective surface 20 and a shroud axis 22. Lines indicating a vertical axis 24 and a horizontal axis 26 are depicted. Such axes 24 and 26 are normal to shroud axis 22.

In an exemplary embodiment of the present invention, conveyor 120 and shroud 16 are configured and operated such that article trajectory 102 passes through shroud 16. The article trajectory 102 is essentially parallel at any location on the trajectory 102 to shroud axis 22.

Article inlet slot 30 and article outlet slot 32 are provided in shroud 16. In the exemplary embodiment, inlet slot 30 and outlet slot 32 are elongated openings in shroud wall 18, each extending parallel to shroud axis 22. Slots 30 and 32 extend beyond the lateral edges (not shown) of article trajectory 102.

In the illustrative embodiment depicted in FIG. 1, inlet slot 30 is located above horizontal axis 26. Outlet slot 32 is located below horizontal 26 on the opposite side of shroud 16, as divided by vertical axis 24, from inlet slot 30. Locations of slots 30 and 32 on shroud 16 may require adjustment depending on the specific gravity of articles to be viewed. Such adjustments may be achieved by rotation of shroud 16 about shroud axis 22 or by altering placement of the slots 30 and 32. The width of slots 30 and 32 are maintained at a minimum level to allow unimpeded flow of articles while maintaining maximum reflective surface area of reflective surface 20.

In a preferred embodiment of the invention, inlet slot 30, outlet slot 32 and article trajectory 102 are arranged such that article trajectory 102 coincides with shroud axis 22.

A scanning slot 34 is provided in shroud wall 18. In the exemplary embodiment, scanning slot 34 is a linear or elongated opening parallel to shroud axis 22. Scanning slot 34 is structured to allow a scanning receptor 50 to identify predetermined characteristics of articles to be scanned and sorted. Receptor 50 may comprise a single receptor or a plurality of receptors.

Referring to FIG. 2, receptor 50 is spaced from scanning slot 34. Receptor 50 is focused along a scanning axis 38. The intersection of scanning axis 38 with trajectory 102 identifies a scan line 23 of articles to be inspected. Scan line 23 coincides with or is near to shroud axis 22. In a preferred embodiment, a plurality of receptors 50 are arranged parallel to scanning slot 34 along the lateral length of article trajectory 102.

A receptor shroud 35 extends intermediate shroud wall 18 and receptors 50. Receptor shroud 35 provides a closed environment between scanning slot 34 and receptor 50 to limit ingress of environmental light intermediate receptor 50 and scanning slot 34. Receptor shroud 35 is preferably provided with a non-reflective interior surface 33.

A plurality of light sources 12 are provided within shroud 16. In the illustrative embodiment depicted, light sources 12 comprise four elongated bulbs aligned parallel to shroud axis 22. Any number of light sources 12 may occupy the housings consistent with a physical limitation that they not impede flow path 102 or scan axis 38.

Reflective surface 20 is provided on the interior of shroud wall 18. Reflective surface 20 comprises a reflective coating having spectral properties suitable for optimal reflection of the illumination energy within the shroud 16. Reflective surface 20 further comprises the background viewed by receptor 50 of the articles to be sorted. The reflective surface 20 coating to be applied in any particular application will be optimized to provide spectral contrast between such background and the characteristics of the material to be viewed taking into account the wavelength emitted by the light sources 12.

Figure 4:
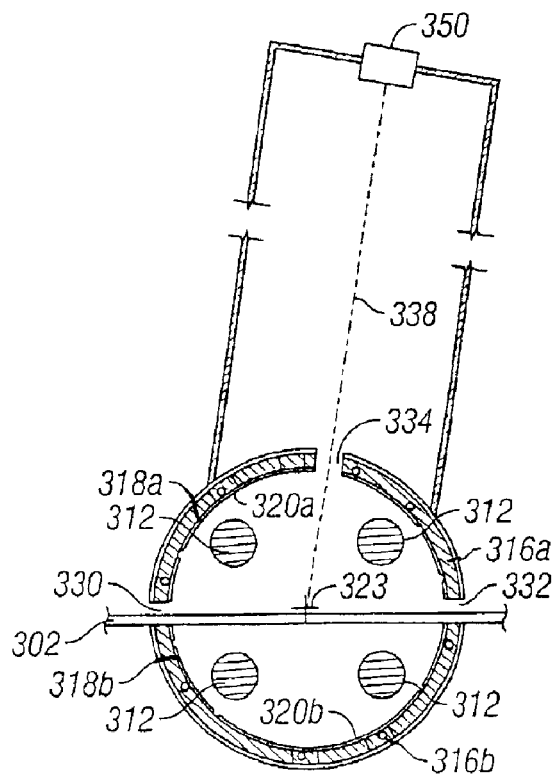
FIG. 4 depicts a cross-sectional view of an alternate embodiment of the illumination system of the present invention.

The elongated light sources 12 depicted in FIGS. 2–4 are arranged parallel to shroud axis 22. Each of light sources 12 is located close to shroud wall 18, yet sufficiently spaced away from shroud wall 18, to allow for reflection of light generated by each of light source 12 distal from shroud axis 22 to be reflected by cylinder reflective surface 20. Light sources 12 are spaced from each other around shroud wall 18 interior of shroud 16.

In the exemplary embodiment, light sources 12 are equally distant from shroud axis 22. The light sources 12 are not themselves focused in an orientation direction, but instead are high intensity, diffused light sources. The diffused light is thus reflected by the reflective surface 20 to create intense light within shroud 16. As the light sources 12 project light radially and as the light sources 12 are contained within a cylindrical wall 18, the light generated by the plurality of light sources 12 will be continuously reflected within cylinder 18. In the scan line 23 adjacent shroud axis 22, intense light will accordingly be received from all directions, including light from light sources 12 and reflected light from reflective surface 20, such that scan line 23 will accordingly receive intense light from all directions.

Light sources 12 may include fluorescent tubes, an array of filament lights, arc lamps, gas discharge lamps, or an array of light-producing semiconductors such as light-emitting diodes. In an alternative embodiment incorporating such alternate light sources 12, the light sources 12 would be arranged near the shroud wall 18 but spaced therefrom and spaced from shroud axis 22, so as to cumulatively provide intense light at the scan line 23, such light to include light directly from light sources 12 and reflected light from reflective surface 20.

The diameter of the cylindrical shroud 16 is limited to the minimum size practicable to maximize illumination intensity at the scan line and to allow placement of ejectors as close as practicable to the scan line to allow more accurate rejection of selected particles. However, the cylinder diameter must be large enough to reduce unwanted effects of removed cylinder surface in the area of the slots.

To further improve uniformity of illumination, the shroud 16 is constructed longer than the required passage area for articles to be inspected. Shroud wall 18 extends laterally along axis 22 beyond the lateral edges of trajectory 122, so that there exists ample reflective surface 20 to fully illuminate the end product particles in trajectory 122.

In the exemplary embodiment depicted, cylinder ends 40 are provided at opposed ends of shroud wall 18. If provided, cylinder ends 40 are each covered with inner reflective surface 20.

In an embodiment comprising elongated bulb light sources 12 as depicted in FIGS. 1 and 2, cylinder ends 40 are placed at the termination of the light-producing segment of the bulb with the non-light-producing connector extending outside the cylinder end 40. Such placements of cylinder ends 40 enhance reflection within shroud 16 and eliminate any adverse effect of the connector or connector base having a differing spectral surface.

Referring to FIGS. 1–3, in an embodiment of the present invention, selector 130 comprises a series of nozzles 134 for selective intermittent ejection of compressed air 131 into trajectory 102. Nozzles 134 form a line along article trajectory 102, such that any individual piece of product (not shown) identified to be sorted may be diverted to trajectory 102b without diverting unidentified pieces of product.

In operation, upon flow of a quantity of articles along trajectory 102 through vision system 10, receptor 50 obtains optical data in relation to an article passing along scan line 23 and transmits such data to a processing means for determination whether the acquired data is within a range of acceptable levels or outside such range. If the data is outside an acceptable range, selector 130 is engaged to eject compressed air 131 at articles in trajectory 102 at a particular point along trajectory 102, thereby changing the trajectory of the identified falling article. For illustration purposes, the trajectory of a rejected article is depicted as 102b and the trajectory of an article that is not rejected is depicted as 102a. In normal operation, selector 130 is timed in relation to article flow past scan line 23 such that the nozzle 134 ejects a short duration blast of compressed air to re-direct the rejected article.

The machine vision system 10 of the present invention is useful in a variety of applications to identify measuring characteristics of an article. The high and relatively even intensity of illumination within shroud 16 at scan line 23, makes the present invention particularly useful in identifying flaws in transparent articles, such as plastic pellets.

In an application involving a transparent article such as a plastic pellet, a characteristic to be scanned, and upon which sorting is conducted, is the existence of contaminants in the article. Transparent articles involve a lensing effect wherein light variations exterior to the article may be reflected by the article. The present invention minimizes such lensing effect in part by providing relatively small inlet slot 30, outlet slot 32 and viewing slot 34, but more importantly by providing the surrounding cylindrical reflective surface 20 with a plurality of diffuse light sources 12 disposed within the shroud 16 to maintain the intensity of light within the shroud 16, thereby producing a balanced, multi-directional light at the scan line 23.

A method of determining an opaque contaminant is to determine the deviation of the total quantity of light intensity as measured at receptor 50 as the article passes through scan line 23. An opaque contaminant absorbs a certain level of illumination resulting in a lower illumination reading by the receptor than the reading for an article that contains no contaminant. The machine vision system 10 of the present invention produces illumination levels at scan line 23 that are not distorted by shadows created by uneven lighting and surface imperfections of the article to be scanned and sorted.

Referring now to FIG. 3, an alternative embodiment of the present invention is depicted. The embodiment of FIG. 3 provides an article trajectory 202 of articles that are in free fall from an inclined gravity slide 201. FIG. 3 depicts two elongated arc shrouds 216a and 216b, which may be collectively referred to as the shroud 216.

Arc shrouds 216a and 216b are constructed as arcs of a hollow cylinder and have a common radius. A central axis 222 is defined at the radial center of shrouds 216a and 216b. Article inlet opening 230 and article outlet opening 232 are defined by the open space between adjacent edges of arc shrouds 216a and 216b.

A viewing slot 234 is provided in shroud 216a, along with a receptor 250 aligned to have a viewing axis 238, as in the embodiment of FIGS. 1–2. A scan line 223 is defined at the intersection of viewing axis 238 and article trajectory 202. As in the embodiment of FIGS. 1–2, a plurality of light sources 212 are provided interior of shrouds 216a and 216b. Reflective inner surfaces 220a and 220b are provided on shrouds 216a and 216b. Light sources 212 are arranged parallel to the scan line 223 and spaced around the interior walls 218a and 218b. In the manner previously described, the light provided by light sources 212 creates an intense level of light from multiple directions at the scan line 223, including direct light from light sources 212 and reflected light from surfaces 220a and 220b.

Referring now to FIG. 4, a second alternative embodiment of the present invention is depicted. In the embodiment of FIG. 4, the articles to be scanned are supported on a spectrally suitable, clear panel 302, such as glass, between two elongated arc shrouds 316a and 316b, which may be referred to collectively as shroud 316. Arc shrouds 316a and 316b are constructed as arcs of a hollow cylinder and have a common radius. A central axis 322 is defined at the radial center of shrouds 216a and 216b.

Article inlet opening 330 and article outlet opening 332 are defined by the open space between the adjacent edges of arc shrouds 316a and 316b. A viewing slot 334 is provided in shroud 316a and a receptor 350, which is aligned to have a viewing axis 338, as in the embodiment of FIGS. 1 and 2. A scan line 323 is defined as the intersection of viewing axis 338 and panel 302. As in the embodiment of FIGS. 1–3, a plurality of high intensity light sources 312 are provided interior of shrouds 316a and 316b, and reflective inner surfaces 320a and 320b are provided on shrouds 316a and 316b. The light sources 312 are arranged parallel to the scan line 323, and spaced from the interior walls 318a and 318b. In the manner previously described, the light provided by light sources 312 creates an intense level of light from multiple directions at the scan line 323, including direct light from light sources 312 and reflected light from surfaces 320a and 320b.

Figure 5:
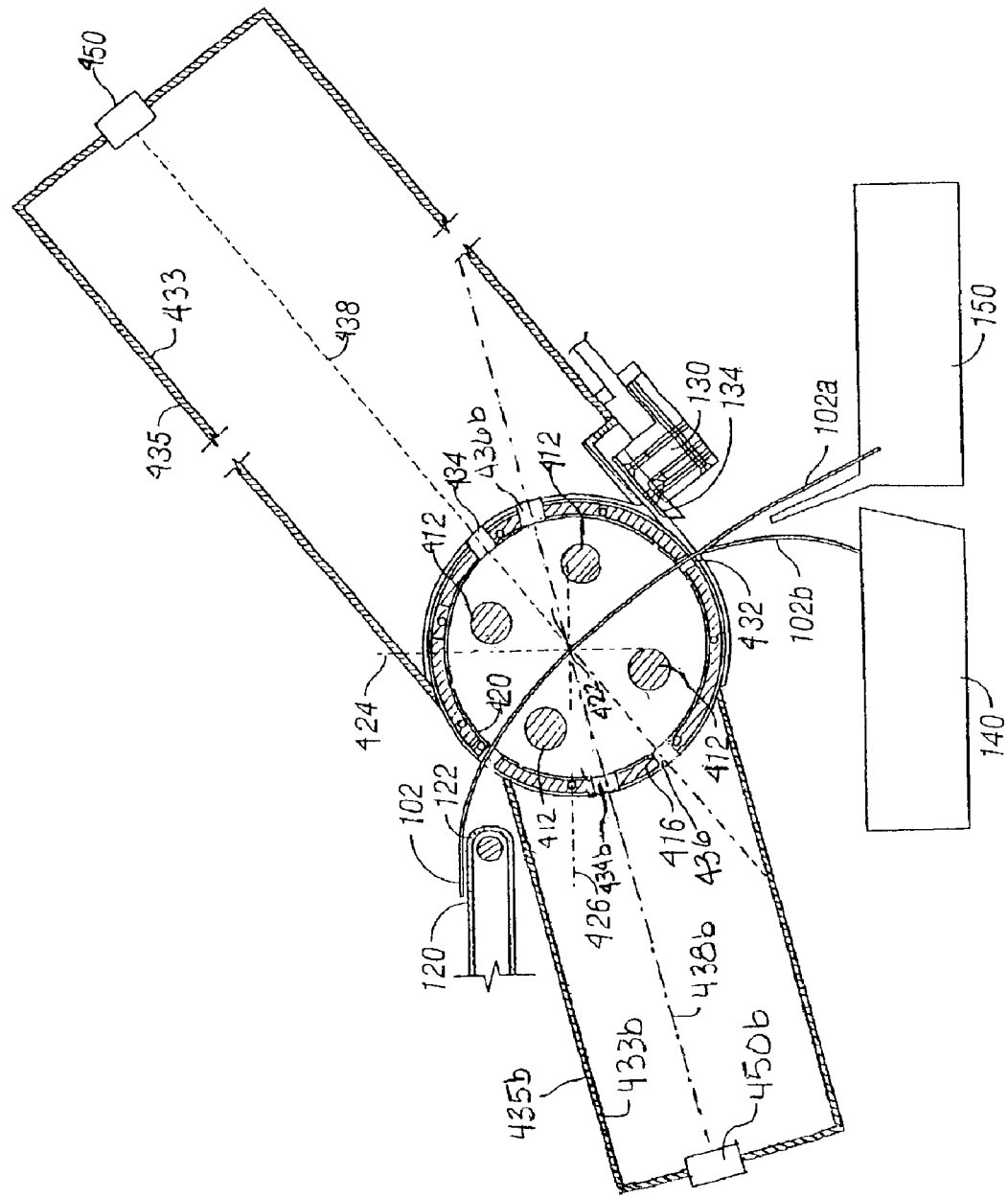
FIG. 5 depicts a cross-sectional view of an alternate embodiment of the illumination system of the present invention.

Referring to FIG. 5, a third alternative embodiment is depicted. This embodiment includes a second scanning slot 434b located in shroud 416 on the opposite side of vertical axis 424 from scanning slot 434. Scanning slot 434b, like scanning slot 434, is an elongated opening parallel to shroud axis 422. Second scanning slot 434b is structured to allow a second scanning receptor 450b to identify predetermined characteristics of articles to be scanned and sorted. Receptor 450b may comprise a single receptor or a plurality of receptors. A plurality of views are provided by receptors 450 and 450b. The views may be compared using a processor or used individually to identify predetermined characteristics of articles.

Receptor 450b is focused along a scanning axis 438b. Receptors 450 and 450b are not directly opposed as it is preferred the scanning axes 438 and 438b are offset at an angle to avoid interference or reflection between receptors 450 and 450b.

A background opening 436 is located in shroud 416 along scanning axis 438 opposite viewing slot 434. A second background opening 436b is located in shroud 416 along scanning axis 438b opposite viewing slot 434b. Background openings 436 and 436b are elongated openings parallel to shroud axis 422. Background opening 436 provides an opening to a receptor shroud 435b, which has a non-reflective inner surface 433b. Thus, receptor 450 has a non-reflective background against which to scan articles. Use of a non-reflective background minimizes any distortion from reflective surfaces when scanning articles. Background opening 436b provides an opening to receptor shroud 435, which also has a non-reflective inner surface 433. Thus, receptor 450b also has a non-reflective background against which to scan articles.

Depending upon the angle between scanning axes 438 and 438b, scanning slot 434 and background opening 436b may be combined into a single slot (not shown) to be used for both scanning and providing a non-reflective background. Likewise, scanning slot 434b and background opening 436 may be so combined.

Although the drawings depict scanning axes 438 and 438b intersecting at a single scan line 523, this embodiment may be practiced with each of the scanning axes 438 and 438b of the intersecting the flow of articles at distinct locations on flow line 102.

Figure 6:
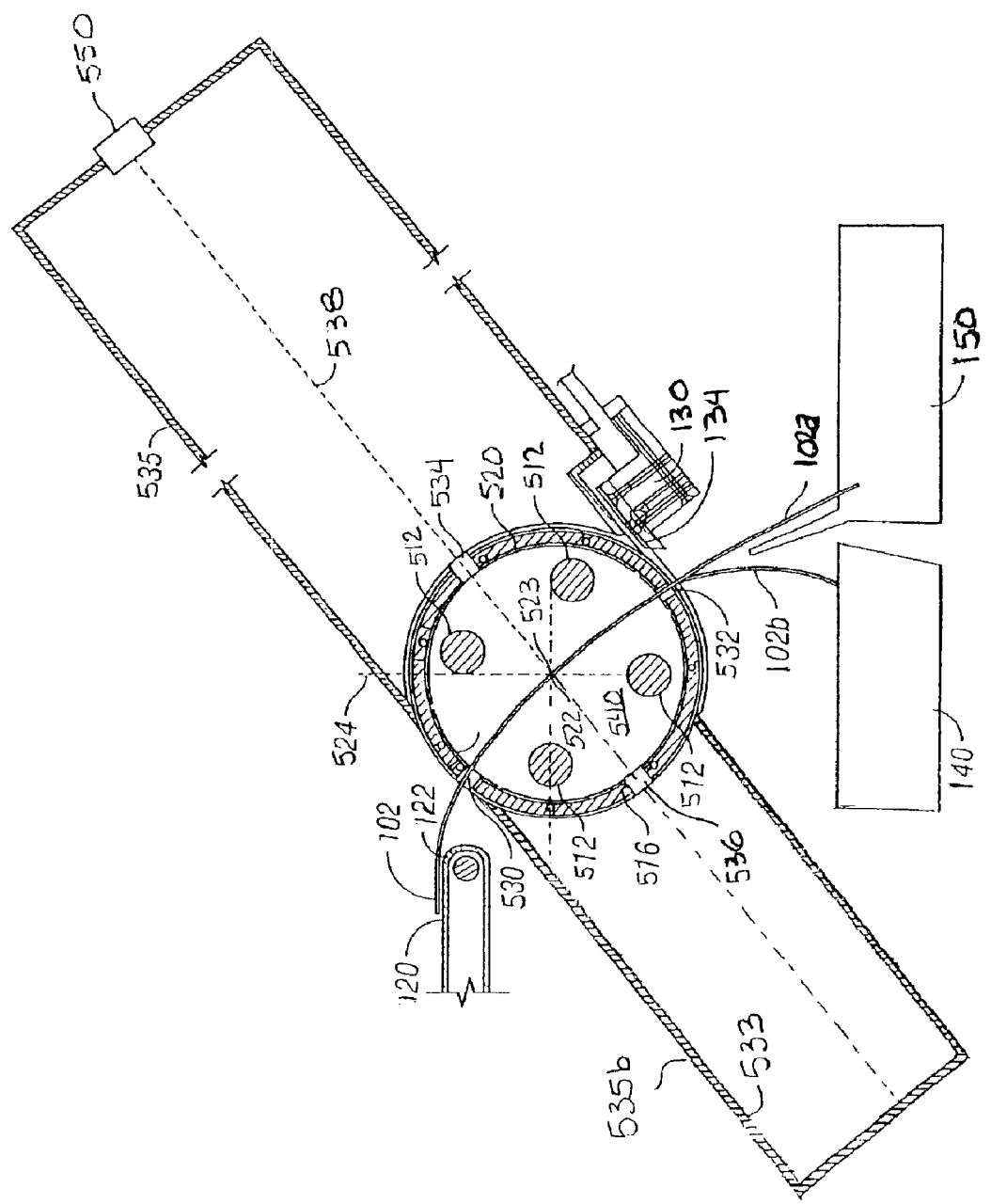
FIG. 6 depicts a cross-sectional view of an alternate embodiment of the illumination system of the present invention.

Referring to FIG. 6, a fourth alternative embodiment is depicted. In this embodiment, a background opening 536 is located in shroud 516 along scanning axis 538 opposite viewing slot 534. Background opening 536 is an elongated opening parallel to shroud axis 522. Background opening 536 provides an opening to a background shroud 535b, which has a non-reflective inner surface 533. Thus, receptor 550 has a non-reflective background against which to scan articles. The non-reflective background minimizes any distortion that may occur when scanning articles.

The foregoing disclosure and description of the invention is illustrative and explanatory thereof. Various changes in the details of the illustrated process may be made within the scope of the appended claims without departing from the spirit of the invention. The present invention should only be limited by the following claims and their legal equivalents.

What is claimed is:

1. An illumination source for a machine vision sorting machine, comprising:

a shroud having an elongated, generally cylindrical shroud wall;

said shroud having a central shroud axis;

said shroud wall having an interior reflective surface;

an article inlet slot in said shroud wall;

an article outlet slot in said shroud wall;

at least one viewing opening in said shroud wall; and at least one light source located intermediate said shroud and said shroud axis, said shroud axis horizontally oriented;

said article inlet slot and said article outlet slot each horizontally elongated;

said article inlet slot located above said shroud axis; and said article outlet slot located below said shroud axis.

2. An illumination source in accordance with claim 1, wherein:

said article inlet slot arranged to allow a flow of articles into said shroud and said article outlet slot arranged to allow a flow of articles from said shroud such that the flow of articles may pass near said shroud axis.

3. An illumination source in accordance with claim 1, wherein:

said article inlet slot and said article outlet slot arranged to allow a flow of articles through said shroud such that said flow of articles may pass through said shroud axis.

4. An illumination source in accordance with claim 1, further comprising:

said light source comprising a plurality of elongated light bulbs;

each said plurality of light bulbs positioned parallel to said shroud axis; and said plurality of light bulbs angularly spaced around said shroud axis.

5. An illumination source in accordance with claim 4, further comprising:

each said plurality of light bulbs spaced from said shroud wall; and each said plurality of light bulbs spaced from said shroud axis.

6. An illumination source in accordance with claim 4, further comprising:

said light source comprising a plurality of bulbs positioned in arrays;

each said array parallel to said shroud axis and angularly spaced around said shroud axis; and each said array spaced from said shroud wall and spaced from said shroud axis.

7. An illumination source in accordance with claim 4, further comprising:

said light source comprising a plurality of light-emitting semiconductors positioned in arrays;

each said array parallel to said shroud axis and angularly spaced around said shroud axis; and each said array spaced from said shroud wall and spaced from said shroud axis.

8. An illumination source in accordance with claim 1, wherein:

said at least one viewing opening in said shroud wall positioned in a first section of said shroud wall;

a second opening in a second section of said shroud wall;

a receptor shroud covering said first viewing opening;

a first receptor located in said receptor shroud;

a background shroud covering said opposed second opening; and said receptor shroud and said background shroud each having a non-reflective inner surface; and said second opening and said background shroud providing a non-reflective background for said receptor.

9. An illumination source in accordance with claim 1, wherein said at least one viewing opening in said shroud wall further comprises:

a first viewing opening in a first section of said shroud wall;

a second viewing opening in a second section of said shroud wall;

a first receptor shroud covering said first viewing opening;

a second receptor shroud covering said second viewing opening;

a first receptor located in said first receptor shroud;

a second receptor located in said second receptor shroud; and each said first receptor shroud and said second receptor shroud having a non-reflective inner surface.

10. An illumination source in accordance with claim 9, further comprising:

a first background opening in said second shroud wall section;

said second receptor shroud covering said first background opening;

a second background opening in said first shroud wall section;

said first receptor shroud covering said second background opening;

said first background opening and said second receptor shroud providing a non-reflective background for said first viewing opening; and said second background opening and said first receptor shroud providing a non-reflective background for said second viewing opening.

11. An illumination source for a machine vision sorting machine, comprising:

a first shroud and a second shroud;

said first shroud comprising a first shroud wall, said first shroud wall comprising an arc of an elongated, hollow cylinder;

said first shroud having a first shroud axis;

said second shroud comprising a second shroud wall, said second shroud wall comprising an arc of an elongated, hollow cylinder;

said second shroud having a second shroud axis;

each said first shroud wall and said second shroud wall having an interior reflective surface;

said first shroud and said second shroud arranged to define a generally cylindrical shroud structure having a first opening and a second opening between said first shroud and said second shroud;

said first shroud opening comprising an article inlet opening;

said second shroud opening comprising an article outlet opening;

at least one viewing opening in one of said first shroud wall or said second shroud wall;

at least one light source located intermediate said first shroud and said first shroud axis; and at least one light source located intermediate said second shroud and said second shroud axis.

12. An illumination source in accordance with claim 11, wherein:

said first shroud axis coincident with said second shroud axis;

said first shroud axis and said second shroud axis horizontally oriented;

said article inlet opening and said article outlet opening each horizontally oriented;

said article inlet opening above said shroud axis; and said article outlet opening located below said shroud axis.

13. An illumination source in accordance with claim 11, further comprising:

said article inlet opening arranged to allow a flow of articles into said shroud, said article outlet opening arranged to allow a flow of articles from said shroud such that the flow of articles passes near said first and second shroud axes.

14. An illumination source in accordance with claim 12, further comprising:

said article inlet opening arranged to allow a flow of articles into said shroud, said article outlet opening arranged to allow a flow of articles from said shroud such that the flow of articles passes though first and second shroud axes.

15. An illumination source in accordance with claim 11, further comprising:

said light source comprising a plurality of elongated light bulbs;

each said plurality of light bulbs positioned parallel to said shroud axis; and said plurality of light bulbs angularly spaced around said shroud axis.

16. An illumination source in accordance with claim 15, further comprising:

each said plurality of light bulbs spaced from said shroud wall; and each said plurality of light bulbs spaced from said shroud axis.

17. An illumination source in accordance with claim 11, further comprising:

said light source comprising a plurality of bulbs positioned in linear arrays;

each said linear array parallel to said shroud axis and angularly spaced around said shroud axis; and each said linear array spaced from said shroud wall and spaced from said shroud axis.

18. An illumination source in accordance with claim 11, further comprising:

said light source comprising a plurality of light-emitting semiconductors positioned in linear arrays;

each said linear array parallel to said shroud axis and angularly spaced around said shroud axis; and each said linear array spaced from said shroud wall and spaced from said shroud axis.

19. An illumination source in accordance with claim 11, wherein said at least one viewing opening in one of said first shroud wall or second shroud wall further comprises:

a first viewing opening in said first shroud wall;

a second viewing opening in said second shroud wail;

a first receptor shroud covering said first viewing opening;

a second receptor shroud covering said second viewing opening;

a first receptor located in said first receptor shroud;

a second receptor located in said second receptor shroud; and said first receptor shroud and said second receptor shroud each having a non-reflective inner surface.

20. An illumination source in accordance with claim 19, further comprising:

a first background opening in said second shroud wall;

said second receptor shroud covering said first background opening;

a second background opening in said first shroud wall;

said first receptor shroud covering said second background opening;

said first background opening providing a non-reflective background for said first receptor; and said second background opening providing a non-reflective background for said second receptor.

21. An illumination source in accordance with claim 11, further comprising:

at least one background opening in one of said first shroud wall or said second shroud wall;

at least one background shroud covering each of said at least one background opening;

said background shroud having a non-reflective inner surface;

a receptor external said shroud wall; and said at least on background opening providing a non-reflective background for said at least one viewing opening.

22. An illumination source in accordance with claim 11, further comprising:

a clear panel extending through said article inlet opening and said article outlet opening for supporting articles in a preferred location.

23. A machine vision sorting machine, comprising:

a hopper;

a conveyor;

a vision system;

a selector;

said vision system comprising a shroud and a receptor;

said shroud comprising an elongated, generally cylindrical shroud wall;

said shroud having a central shroud axis;

said shroud oriented horizontally;

said shroud wall having an interior reflective surface;

an article inlet slot in said shroud wall;

an article outlet slot in said shroud wall;

said article inlet slot said article outlet slot each horizontally elongated;

said article inlet slot located above said shroud axis; and said article outlet slot located below said shroud axis, at least one viewing opening in said shroud wall; and at least one light source located intermediate said shroud wall and said shroud axis.

24. An illumination source in accordance with claim 23, further comprising:

a gravity slide intermediate said conveyor and said vision system.

25. An illumination source in accordance with claim 23, further comprising:

said conveyor, said article inlet slot and said article outlet slot located to allow a free flow of articles passing near the shroud axis; and said receptor and said viewing opening located to allow scanning of a flow of articles near the shroud axis.

26. An illumination source in accordance with claim 23, further comprising:

said conveyor, said article inlet slot and said article outlet slat located to allow a free flow of articles passing through the shroud axis; and said receptor and said viewing opening located to allow scanning of a flow of articles at said shroud axis.

27. An illumination source in accordance with claim 23, further comprising:

said article inlet slot and said article outlet slot each extending the full length of the shroud wall such that the shroud wall comprises two disconnected shroud wall segments;

said conveyor, said article inlet slot and said article outlet slot located to allow a free flow of articles passing near the shroud axis; and said receptor and said viewing opening located to allow scanning of a flow of articles near the shroud axis.

28. An illumination source in accordance with claim 23, further comprising:

said article inlet slot and said article outlet slot each extending the full length of the shroud wall such that the shroud wall comprises two disconnected shroud wall segments;

said conveyor, said article inlet slot and said article outlet slot located to allow a free flow of articles passing through the shroud axis; and said receptor and said viewing opening located to allow scanning of a flow of articles at the shroud axis.

29. An illumination source in accordance with claim 23, further comprising:

said light source comprising a plurality of elongated light bulbs;

each said plurality of light bulbs positioned parallel to said shroud axis;

said plurality of light bulbs angularly spaced around said shroud axis;

each said plurality of light bulbs spaced from said shroud wall; and each said plurality of light bulbs spaced from said shroud axis.

30. An illumination source in accordance with claim 23, further comprising:

said light source comprising a plurality of light sources positioned in linear arrays;

each said linear array parallel to said shroud axis and angularly spaced around said shroud axis; and each said linear array spaced from said shroud wall and spaced front said shroud axis.

31. An illumination source in accordance with claim 23, wherein:

said at least one viewing opening in said shroud wall comprises a first viewing opening in a first shroud wall section and a second viewing opening in a second shroud wall section;

a first viewing cover coveting said first viewing opening;

a first receptor in said first viewing cover;

a second viewing cover covering said second viewing opening;

a second receptor in said second viewing cover; and said first viewing cover and said second viewing cover each having a non-reflective inner surface.

32. An illumination source in accordance with claim 23, further comprising:

a first background opening in said second shroud wall section;

said second viewing cover covering said first background opening;

a second background opening in said first shroud wall section;

said first viewing cover covering said second background opening;

said first background opening and said second viewing cover providing a non-reflective background for said first receptor; and said second background opening and said first viewing cover providing a non-reflective background for said second receptor.

33. An illumination source in with claim 23, further comprising:

at least one background opening in said shroud wall;

at least one background cover covering each of said at least one background opening;

said background cover having a non-reflective inner surface;

at least one receptor;

said viewing opening intermediate said receptor and said background opening; and said at least on background opening and said background cover non-reflective inner surface providing a non-reflective background for said at least one receptor.

34. A method of sorting particulate material comprising:

establishing a flow of articles to be inspected;

flowing said articles near a horizontally oriented central axis of an elongated, horizontally-positioned cylindrical shroud, said shroud having a horizontally elongated article inlet slot located above said horizontally oriented central axis and a horizontally elongated article outlet slot located located below said horizontally oriented central axis, providing a reflective surface on the interior of said shroud;

providing a diffuse, high intensity light field interior of said cylindrical shroud at said shroud axis;

scanning articles passing through aid cylindrical shroud as said articles pass near said shroud axis;

determining articles to be separated from the article flow; and diverting maid determined articles.

35. A method of according to claim 34, wherein:

said establishing step comprising conveying said articles to a determined location and allowing free fall of said articles;

said scanning step comprising receiving reflected light waves from said articles;

said determining step comprising processing data from said reflected light waves, processing said data, and transmitting separating instructions to a diverting mechanism; and said diverting step comprises blowing directed air at said determined article.

36. A method of according to claim 34 wherein:

providing said diffuse, high intensity light field comprises providing a plurality of high intensity, diffused light sources spaced from said cylindrical shroud and spaced from said shroud axis.

* * * * *

UNITED STATES PATENT AND TRADEMARK OFFICE
CERTIFICATE OF CORRECTION

PATENT NO. : 6,936,784 B2
APPLICATION NO. : 10/444195
DATED : August 30, 2005
INVENTOR(S) : Robert Ogburn et al.

It is certified that error appears in the above-identified patent and that said Letters Patent is hereby corrected as shown below:

Column 12, line 19, "24. An illumination source in accordance with claim 23," should be changed to --24. A machine vision sorting machine in accordance with claim 23,--.

Column 12, line 23, "25. An illumination source in accordance with claim 23," should be changed to --25. A machine vision sorting machine in accordance with claim 23,--.

Column 12, line 30, "26. An illumination source in accordance with claim 23," should be changed to --26. A machine vision sorting machine in accordance with claim 23,--.

Column 12, line 37, "27. An illumination source in accordance with claim 23," should be changed to --27. A machine vision sorting machine in accordance with claim 23,--.

Column 12, line 48, "28. An illumination source in accordance with claim 23," should be changed to --28. A machine vision sorting machine in accordance with claim 23,--.

Column 12, line 59, "29. An illumination source in accordance with claim 23," should be changed to --29. A machine vision sorting machine in accordance with claim 23,--.

Column 13, line 9, "30. An illumination source in accordance with claim 23," should be changed to --30. A machine vision sorting machine in accordance with claim 23,--.

Column 13, line 17, "31. An illumination source in accordance with claim 23," should be changed to --31. A machine vision sorting machine in accordance with claim 23,--.

Column 13, line 30, "32. An illumination source in accordance with claim 23," should be changed to --32. A machine vision sorting machine in accordance with claim 23,--.

UNITED STATES PATENT AND TRADEMARK OFFICE
CERTIFICATE OF CORRECTION

PATENT NO. : 6,936,784 B2
APPLICATION NO. : 10/444195
DATED : August 30, 2005
INVENTOR(S) : Robert Ogburn et al.

It is certified that error appears in the above-identified patent and that said Letters Patent is hereby corrected as shown below:

Column 13, line 46, "33. An illumination source in accordance with claim 23," should be changed to --33. A machine vision sorting machine in accordance with claim 23,--.

Signed and Sealed this

Fourteenth Day of August, 2007

JON W. DUDAS
*Director of the United States Patent and Trademark Office*